United States Patent [19]

Lyons

[11] Patent Number: 4,602,103

[45] Date of Patent: Jul. 22, 1986

[54] PROCESS FOR THE OXIDATION OF BUTENES TO LINEAR ACETATES

[75] Inventor: James E. Lyons, Wallingford, Pa.

[73] Assignee: Sun Refining and Marketing Company, Philadelphia, Pa.

[21] Appl. No.: 721,627

[22] Filed: Apr. 10, 1985

Related U.S. Application Data

[63] Continuation-in-part of Ser. No. 664,566, Oct. 29, 1984, abandoned, which is a continuation-in-part of Ser. No. 559,139, Dec. 7, 1983, abandoned.

[51] Int. Cl.$^4$ .............................................. C07C 67/05
[52] U.S. Cl. ................................... 560/243; 568/858; 568/864
[58] Field of Search ....................... 560/244, 243, 245; 568/858, 864

[56] References Cited

U.S. PATENT DOCUMENTS

| | | | |
|---|---|---|---|
| 3,850,980 | 11/1974 | Clarke | 560/243 |
| 3,872,163 | 3/1975 | Shimizu | 560/244 |
| 3,970,713 | 7/1976 | Scharfe | 560/245 |
| 4,150,239 | 4/1979 | Tanabe | 560/244 |
| 4,225,729 | 9/1980 | Toriya | 560/244 |

FOREIGN PATENT DOCUMENTS

| | | | |
|---|---|---|---|
| 1238459 | 4/1967 | Fed. Rep. of Germany | 560/243 |
| 969017 | 9/1964 | United Kingdom | 560/244 |

OTHER PUBLICATIONS

Hartley, "The Chemistry of Platinum and Palladium," pp. 386–390 & 412–417 (1973).

Primary Examiner—Michael L. Shippen
Attorney, Agent, or Firm—J. Edward Hess; Donald R. Johnson; Stanford M. Back

[57] ABSTRACT

$C_4$ olefins comprising cis- and trans-butane-2 and butene-1 may be oxidized to their corresponding mono- and diacetates in the presence of acetic acid and an olefin-activated palladium catalyst under mild conditions. With this catalyst, and depending in part upon the solvent employed, as well as other operating conditions, the formation of linear allylic 1-acetates over the corresponding branched compounds can be favored in order to increase the yield of the corresponding linear 1,4-diacetates. The latter, in turn, may then be converted, for example, to butanediol by known hydrogenation methods.

In a similar manner, isobutylene may be converted to a dialcohol.

28 Claims, No Drawings

PROCESS FOR THE OXIDATION OF BUTENES TO LINEAR ACETATES

CROSS-REFERENCE TO RELATED CASES

This application is a continuation-in-part of U.S. application Ser. No. 664,566, filed Oct. 29, 1984, now abandoned, which in turn is a continuation-in-part of U.S. application Ser. No. 559,139, filed Dec. 7, 1983, now abandoned, in the name of James E. Lyons.

The subject matter of this invention, is related to that of Ser. No. 721,817, filed April 10, 1985 in the names of Lyons, et al. and entitled "Catalytic Oxidation of Olefins to $\alpha,\beta$-Unsaturated Carboxylic Acids".

BACKGROUND OF THE INVENTION

1. Field of the Invention

This invention relates to the formation of certain linear diacetates from their respective $C_4$ olefins. More particularly, this invention relates to the oxidation of certain defined $C_4$ olefins under conditions which favor the formation of the corresponding linear 1,4-diacetates over the branched diacetates, and converting the said linear 1,4-diacetates to butanediol, employing a novel olefin-activated palladium metal catalyst.

In a like manner, isobutylene may be converted to the corresponding branched alcohol and isomeric butanediols.

2. Description of the Prior Art

P. M. Henry (J. Org. Chem. 32, 2575 (1967), describes the oxidation of butene-1 and cis-and trans-butene-2 to their respective chloroacetates and diacetates, using a catalyst system comprised of palladium acetate, cupric chloride, and lithium acetate at temperatures of about 100° C. and at maximum olefin pressure. The yield of diacetates, however, is below 20 percent, and of linear 1,4-diacetates is below 0.4 percent.

Shimizu, U.S. Pat. No. 3,872,163, describes the oxidation of various $C_4$'s, particularly butadiene, to form butene diacetates employing conventional palladium catalysts, preferably in the presence of certain metal acetates. The use of applicant's unique olefin-activated palladium, described herein below is not taught or suggested herein. Hinnenkamp, U.S. Pat. No. 4,435,598; Scharfe, U.S. Pat. No. 3,970,713; and Onoda 4,016,200 also teach conventional methods for oxidizing olefins in the presence of palladium catalysts, wherein said catalysts are prepared by reducing palladium salts with various reducing agents including olefins under routine reduction conditions. Scharfe, whose catalyst is impregnated with potassium acetate for use in oxidizing propylene to allyl acetate, additionally makes the obvious point that it is commercially advantageous, although not essential, to carry out the reduction before introducing the volumes of oxygen needed for oxidation. Nowhere, however, is there any recognition of preparing the catalyst in the substantial absence of oxygen, or the benefits to be derived therefrom. Similarly, Hartley, "The Chemistry of Platinum and Palladium," Wiley and Sons, pp. 386–390 and 412–417 (1973) discloses a method for making a palladium chloride catalyst complexed with ethylene for use in olefin acetylation to form vinyl acetate. As with Shimizu, however, none of these prior art techniques disclose the use of a unique olefin-activated palladium metal catalyst as defined herein to oxidize butene to form butene diacetates.

It is thus an object of this invention to provide an alternate method for the oxidation of certain butenes to their corresponding linear 1,4-diacetates in increased ratios over the branched diacetates employing a unique olefin-activated palladium catalyst, which diacetates may be converted to butanediol.

These and other objects of the invention will be described in further detail below.

SUMMARY OF THE INVENTION

As briefly outlined above, it is an object of this invention to provide those reaction conditions which optimize the formation of acetates and linear diacetates, from which butanediol may then be obtained. In general, the use of palladium catalysts for the oxidation of cis- and trans-butene-2 and butene-1 favors the formation of branched acetates, and more particularly branched vinylic acetates, together with branched allylic acetates, linear vinylic acetates, and lesser amounts of linear allylic acetates, the latter being the desired intermediates to the corresponding linear 1,4-diacetates which may then be converted to butanediol. Accordingly, those conditions which reduce the formation of branched and/or vinylic intermediates will thus favor the formation and recovery of the desired linear allylic diacetate intermediates.

It has now been found, in accordance with the present invention that these objectives may be achieved, and the formation of linear allylic acetates enhanced, when cis- or trans-butene-2, or butene-1 are oxidized in the presence of a novel olefin-activated, supported palladium catalyst, as further characterized below, and more particularly, when this catalyst is used in combination with certain solvents, at moderate temperatures and pressures, the ratio of the desired linear compounds over the branched and/or vinylic compounds is significantly improved.

That is to say, the formation of the linear allylic acetates and diacetates is favored over the more predominate branched vinylic and allylic acetates in higher proportions than previously described, and under significantly more mild reaction conditions. The resulting linear 1,4-diacetates, after separation from the reaction mixture, may then be converted to butanediol, a valuable article of commerce, by known methods and in high yields.

It will be understood in the foregoing as well as following description that by the term "linear diacetates" is meant 1,4-butene diacetates, whereas the term "branched diacetates" includes the corresponding 1,2-; 1,3-; and 2,3-compound. Likewise, the linear monoacetates refer to the 1-butene acetates, while the branched monoacetates may be either the corresponding 2-or 3-acetate compound.

DESCRIPTION OF THE PREFERRED EMBODIMENTS

The aforedescribed oxidation is desirably carried out in glacial acetic acid, to which the palladium catalyst, whose preparation is described in detail below, is added. As shown in the examples below, metal acetates may also be employed, if desired, for the purpose of increasing the acetate anion concentration and the yield, as well as certain selected solvents which serve to direct the reaction towards the formation of linear acetates and diacetates. The desired $C_4$ olefin, either cis-butene-2, trans-butene-2, or butene-1, is then introduced under pressure mixed with oxygen or air, and the oxidation carried out for the desired period of time, at temperatures of from about 50° to 100° C. The pressure, during the oxidation phase, may be maintained at about 1 to 50 atmospheres, preferably in the range of from about 1 to 10 atmospheres.

After the oxidation has been carried out for the desired period, the reaction mixture is fractionally distilled in order to separate out first the linear and branched, monoacetates, both vinylic and allylic which are then recycled to the reactor, after which the linear allylic diacetates are separated from the branched diacetates. These linear butene 1,4-diacetates may then be hydrogenated in an aqueous medium in either one or two steps to form the desired butanediol. (See E.G., Belgian Pat. No. 834,113 (1976); Japanese Pat. No. 8.1-42569 (1981); or Japanese Pat. No. 093224 (1977), which teach this well-known expedient.)

In one preferred embodiment of this process, in order to increase the reaction rate and at the same time reduce the reactor volume, it has been found to be advantageous that the reaction be carried out in a trickle bed reactor in which the liquid reaction medium is allowed to pass downward over a fixed catalyst bed and the acetate product recovered at the bottom. Alternatively, the oxidation reaction can be carried out using an ebulating bed of catalyst while circulating gases and solvent.

As described in copending application Ser. No. 721,817 with reference to the oxidation propylene, the catalyst employed in this invention may be prepared by activating a carbon- or alumina-supported palladium metal catalyst with a $C_{3-6}$ olefin, preferably, in this case, butene, and most preferably the butene corresponding to the one to be oxidized. The starting material from which the catalyst is prepared may be any finely divided palladium in the metallic state, on a support such as carbon or, less preferred, alumina, as for example a commercially available 5%, 10%, or 20% palladium on carbon available from standard catalyst manufacturers such as Engelhard Industries or Johnson Mathey, Inc. By the terms "palladium metal catalyst" or "palladium in the metallic state" is meant those palladium catalysts which have been prepared from their salts or like compounds by known reduction means either commercially or as shown, for example, by Scharfe et al, U.S. Pat. No. 3,970,713, or Holzrichter et al, U.S. Pat. No. 3,275,680, but which have simultaneously or subsequently been exposed to the atmosphere in normal course of preparing and handling the same. While applicant does not wish to be bound by any particular theories, it is believed that in the normal course of preparing, handling and using the reduced catalysts of the prior art during or subsequent to reduction of the palladium, a certain proportion of the palladium surface species, by virtue of exposure to oxygen or the atmosphere, becomes at least partly oxidized. It is this oxidized form of palladium metal catalyst which is now being employed as the starting material in the preparation of the olefin-activated catalyst employed herein. (By "surface species", as recognized by those skilled in the catalyst art, is meant any species of palladium found at the surface of the catalyst per se.)

Again, while applicant does not wish to be bound by any particular theory, it is believed that when this partly oxidized palladium surface, as described above, is contacted with butene in accordance with applicant's invention, it is first converted to highly active palladium metal sites having zero valence, and it is with these sites that the butene then forms the novel surface-active species which is the activated catalyst used in this invention.

As evidence that the commercially-reduced palladium, for example, has formed oxidized sites on its surface under normal preparation, handling and exposure to air, it has been found that in the course of preparing the novel activated catalyst of this invention, starting, e.g., with a commercially reduced palladium metal catalyst under oxygen-free conditions in water two parts butene employed in activating the catalyst result in the formation of one part of a ketone and one part active catalyst species.

In preparing the novel activated oxidation catalyst of this invention by treating a carbon- or alumina-supported palladium metal catalyst as defined above with propylene or like olefins, it is essential that this activation treatment be carried out under oxygen-free conditions, as described below. Because little or no activation appears to take place below about 50° C., it is also necessary that this activation be conducted at temperatures of greater than about 50° C., desirably from about 55° C. to about 150° C., and preferably from about 60° to 95° C., for a period of time sufficient to provide at least a small but perceptible quantity of said activated catalyst, i.e. one which is highly effective for oxidizing propylene at temperatures of about 25° C. and above. While the time necessary to activate the catalyst is not critical, and will depend upon its nature and amount, generally, periods of at least about 10 minutes, preferably at least about 30 minutes are necessary to produce activation, as defined below. This activation is desirably carried out at pressures of at least about 1 atmosphere, up to about 10 atmospheres of olefin, although about 2–20 atmospheres is preferred. While the activation is desirably conducted in a liquid medium, preferably acetic acid, alternatively it may be carried out in a pure, oxygen-free olefin atmosphere alone, i.e. in the vapor phase. In addition to water or acetic acid, solvents which do not adversely affect the activity of the catalyst may be employed instead.

When these catalysts are thus activated, palladium-on-carbon, for example, which was otherwise far less reactive at temperatures below about 60° C. for purposes of oxidizing butene is now surprisingly active at temperatures of about 25° C. or above. Thus, by the term "activated palladium metal catalyst" is meant, for purposes of this invention, a catalyst prepared in accordance with the above method.

During the preparation of the catalyst, as stated above, it is necessary for purposes of deriving maximum activity from the catalyst that the activation be carried out in the substantial absence of oxygen, and preferably under essentially oxygen-free conditions. While the presence of small amounts of oxygen, to an extent which can be readily determined by those skilled in the art, can still result in a catalyst which performs somewhat better than the commercial catalysts described above, the full benefits of the present invention are derived from activating the catalyst under conditions which are as oxygen-free as possible.

These oxygen-free conditions can be achieved by known means, for example by using deaerated water or acetic acid or solvent, and pure olefin gas, during the activation of the catalyst. Deaeration can be readily achieved by placing the liquid under vacuum until it boils, or by bubbling the desired olefin through the liquid for a period of time until no more oxygen is displaced. The pure olefin can be obtained commercially in various grades such as chemical purity grade, research purity grade, or polymer grade, the latter two being perferred because of their higher purity of over about 99.7%. (The latter two are available, for example from Matheson, Division of Searle Medical Products, and Sun Co., respectively.)

Once applicant's catalyst is formed, it is preferable that at least a slight excess of butene be present at all times to prevent any deactivation, and that desirably during the oxidation step, oxygen in the reactor be maintained in no greater than the stoichiometric amounts needed for the oxidation of the butene to butene acetates and diacetates. It will also be understood that in preparing the catalyst of this invention, the presence of those metals or metal salts which might poison or alter the catalyst should be avoided, for example iron, manganese, copper and rhodium salts; chlorides, benzoquinone, the oxidized form of heteropoly acids, as well as any other agents which would oxidize palladium to palladium$^{+2}$. Other such deleterious materials can be routinely determined by those skilled in the art. For example, in addition, it has been found that such materials as amines, hydrazine, and ethylene should be avoided as deleterious when preparing and using the catalyst of this invention. Moreover, it has been found that attempts to use hydrogen to prepare this catalyst may result in explosions when the catalyst is then exposed to $O_2$-butene mixtures, and should also be avoided.

While the catalyst of the invention may be prepared separately and maintained in an active state if kept in an oxygen-free atmosphere, more conveniently the preparation is carried out in the same reactor used for the butene oxidation. This may conveniently be achieved, for example by adding a commercially available finely divided palladium on activated carbon to an acetic acid medium in a sealed reactor, flushing the system with desired butene gas, and then heating the mixture under butene pressure until the desired temperature for preparation of the catalyst is reached, at which time the mixture is stirred for at least 30 minutes at that temperature, again, in the absence of oxygen, and desirably in the presence of a slight excess of butene.

After the preparation of the catalyst, the selected butene starting material may be replaced by a mixture of said butene and oxygen, desirably with oxygen being present in not greater than approximately stoichiometric amounts to avoid deactivation of the catalyst, and the oxidation reaction carried out in the presence of acetic acid at pressures of from about 1 to 10 atmospheres. The pressure may be maintained by the further addition of the gas mixture from time to time until the desired conversion is achieved. Air may be used in place of oxygen, in which case the amount of butene must be adjusted proportionately.

While the activating agent for the catalyst is preferably the butene to be oxidized, this is not essential, and other light olefins may be used instead, such as propylene, or butenes other than the one to be oxidized.

The olefin-activated catalyst will maintain its activity over long periods of time as long as at least small amounts of an acceptable olefin are present. Thus, it has been found beneficial to run the reaction by constantly sparging the butene/oxygen or air reaction mixture through the acetic acid solution. In this way, the butene is kept in excess and the catalyst remains highly active, thereby maintaining high selectivities and other advantages noted above.

When carrying out the oxidation in a batch-wise manner the ratio of catalyst to reaction medium is desirably in the range of about 0.05–5.0 gram atoms of palladium per liter of reaction medium, and preferably about 0.1–1.0 gram atoms. In a continuous process utilizing, e.g., a fixed bed reactor, the reaction can be conducted effectively by varying the volume of reactants and contact time with the catalyst in a generally known manner to achieve the high yields and selectivities disclosed herein.

Small amounts of a metal acetate such as sodium acetate may be added to the reaction for the purpose of enhancing the acetate anion concentration and the yield, generally in amounts of from about 0.1 to 0.8 moles per liter of medium, and more preferably 0.3 to 0.7 moles/liter.

In a further aspect of this invention, it has been found that when certain solvents are employed in addition to acetic acid, the ratio of the desired allylic linear acetates and diacetate to branched acetates is further enhanced. Thus, for example, when dioxane, sulfolane or dimethylacetamid is employed, ratios of allylic linear to branched acetates can be improved from about 0.33 to >1.0. The solvents may be added to the glacial acetic acid in amounts of from 10 to 80 volume % and preferably 30 to 60 volume %.

When the oxidation of cis- and trans-butene-2 and butene-1 is carried out in accordance with the present invention there are obtained the aforementioned corresponding allylic and vinylic linear and branched monoacetates and diacetates, as for example cis- and trans-2-butene-1-acetates; 1-butene-4-acetate; 1-butene-3-acetate; cis and trans-2-butene-2 acetates; 1-butene-1-acetate and 1-butene-2-acetate; cis- and trans-1, 4-diacetoxy-2-butene; cis-and trans- diaetoxy-1-butene; and the like, as described in detail in the tables below.

In a further embodiment of this invention isobutene may be oxidized in a like manner to the corresponding linear monoacetate and then hydrolyzed to the corresponding branched alcohol in a known manner.

The invention will now be illustrated by, but is not limited to, the following examples.

EXAMPLES

In these examples, several runs were made, employing the procedure set forth below, but varying the solvents, reaction conditions and the like as indicated in the accompanying tables:

An aqueous suspension of 1.0 gram of 10% palladium-on-carbon (Engelhard Industries) in 30 ml. of deaerated glacial acetic acid was activated by stirring in the presence of 4.0 grams of either pure cis- or trans-2-butene (research purity grade) for 30 minutes at 65° C. Metal acetates were also added in some cases as shown in Table 1. After the 30-minute activation period at 65° C., oxygen was added (partial pressure $O_2=5$ atm.) together with the butene, and the mixture was stirred at 65° C. for the time designated. After this period, the reaction mixture was cooled to room temperature, filtered free of the catalyst and analyzed by standardized glpc. Results of the analyses are given in Table 1.

Compounds referred to as linear allylic monoacetates were determined to be the respective cis- and trans-2-butene-1-acetates as well as 1-butene-4-acetate. The branched allylic isomer was shown to be 1-butene-3-acetate. Vinylic acetates included cis- and trans-2-butene-2-acetates and minor amounts of 1-butene-1-and 2-acetates. The linear diacetates are cis- and trans-1, 4-diacetoxy-2-butene and cis- and trans-diacetoxy-1-butene. All other diacetates are referred to in Table 1 as branched.

Products were isolated by distillation and identified by GC-MS, infrared and nmr spectra. Where ambiguity existed their gc and spectral data were compared with authentic samples for positive identification.

In all cases (Examples 1–10) allylic acetates predominated over vinylic acetates by a large margin ($\geq 7/1$) when pre-reduced supported palladium catalysts were used. It was also shown (Examples 1–10) that branched allylic acetates predominate over linear allylic acetates; however, the degree of preference varies depending on the catalyst and reaction conditions.

Examples 1 and 2, using 10% Pd/C, show that branched allylic monoacetates predominate over linear allylic monoacetates by greater than 2.5/1, and branched diacetates predominate over linear diacetates by a 5/1 margin. When reaction was run in the presence of sodium acetate, (Examples 3 & 4) the rate was approximately doubled, but the selectivity was about the same. When the temperature was increased from 65° C. to 82° C. the predominance of branched diacetates over linear diacetates fell to 1.5/1 (Examples 5 & 6).

Reactions catalyzed by 10% Pd/C at 65° C. in the presence of cesium acetate (Examples 7 & 8) gave allylic monoacetates in the same branched to linear ratio as those reactions run in the presence of sodium acetate (Ex. 3 & 4). But, when cesium acetate was used, the ratio of branched to linear dacetate was 1.5. When 10% Pd/Al$_2$O$_3$ was used in place of 10% Pd/C there was little change in product profile (Examples 9 & 10).

TABLE I

THE OXIDATION OF CIS- AND TRANS-2-BUTENE OVER PALLADIUM

| Example | 2-Butene | Catalyst | T °C. | t, hrs. | HOAc, mls | Metal Acetate | mmoles | Gms Acetate Produced | O$_2$ Consumed, psi | SELECTIVITY; GC AREA % MONOACETATES | | |
|---|---|---|---|---|---|---|---|---|---|---|---|---|
| | | | | | | | | | | Linear Allylic | Branched Allylic | Vinylic |
| 1 | CIS | 10% Pd/C | 65 | 6.0 | 30 | — | — | 1.9 | 3.4 | 17.1 | 46.3 | 8.4 |
| 2 | TRANS | 10% Pd/C | 65 | 6.0 | 30 | — | — | 1.2 | 36 | 17.7 | 45.6 | 8.9 |
| 3 | CIS | 10% Pd/C | 65 | 8.0 | 30 | NaOAc | 20 | 2.9 | 70 | 15.4 | 45.1 | 9.0 |
| 4 | TRANS | 10% Pd/C | 65 | 8.0 | 30 | NaOAc | 20 | 4.0 | 101 | 17.9 | 43.2 | 7.2 |
| 5 | CIS | 10% Pd/C | 82 | 7.0 | 30 | NaOAc | 20 | N/A | 196 | N/A | N/A | N/A |
| 6 | TRANS | 10% Pd/C | 82 | 7.0 | 30 | NaOAc | 20 | N/A | 171 | N/A | N/A | N/A |
| 7 | CIS | 10% Pd/C | 65 | 6.0 | 30 | CsOAc | 15 | 3.5 | N/A | 15.3 | 48.4 | 9.8 |
| 8 | TRANS | 10% Pd/C | 65 | 6.0 | 30 | CsOAc | 15 | 2.01 | 54 | 15.2 | 48.4 | 8.0 |
| 9 | CIS | 5% Pd/Al$_2$O$_3$ | 65 | 8.0 | 30 | NaOAc | 20 | 2.4 | 56 | 17.0 | 57.3 | 5.3 |
| 10 | TRANS | 5% Pd/Al$_2$O$_3$ | 65 | 8.0 | 30 | NaOAc | 20 | 3.5 | 75 | 15.1 | 48.5 | 7.4 |

| Example | 2-Butene | Catalyst | SELECTIVITY; GC AREA % | | | | | CO$_2$ Produced % in Gas |
|---|---|---|---|---|---|---|---|---|
| | | | MONOACETATES | | | | DIACETATES | |
| | | | DIACETATES | | Allylic/ Vinylic | Lin. Allylic/ Br. Allylic | Linear/ Branched | |
| | | | Linear | Branched | | | | |
| 1 | CIS | 10% Pd/C | 4.5 | 23.7 | 7.5 | 0.37 | 0.19 | 2.8 |
| 2 | TRANS | 10% Pd/C | (27.8) | | 7.1 | 0.39 | N/A | 0.4 |
| 3 | CIS | 10% Pd/C | 5.2 | 25.3 | 6.7 | 0.34 | 0.21 | 1.0 |
| 4 | TRANS | 10% Pd/C | 5.3 | 26.0 | 8.5 | 0.42 | 0.20 | 1.2 |
| 5 | CIS | 10% Pd/C | N/A | N/A | N/A | 0.64 | N/A | 4.5 |
| 6 | TRANS | 10% Pd/C | N/A | N/A | N/A | 0.67 | N/A | 3.7 |
| 7 | CIS | 10% Pd/C | 10.1 | 16.3 | 8.7 | 0.32 | .062 | 2.4 |
| 8 | TRANS | 10% Pd/C | 11.6 | 16.7 | 8.0 | 0.31 | 0.69 | 0.3 |
| 9 | CIS | 5% Pd/Al$_2$O$_3$ | 8.2 | 11.0 | 14.0 | 0.30 | 0.75 | 1.0 |
| 10 | TRANS | 5% Pd/Al$_2$O$_3$ | 8.0 | 18.9 | 8.6 | 0.31 | 0.46 | 1.1 |

N/A = NOT AVAILABLE

EXAMPLE 11

Using the procedures of Example 3 except that the solvent was changed from 100% acetic acid to a 50/50 mixture of dioxane and acetic acid, yields of vinylic monoacetates decreased to 2%, yields of linear monoacetates increased to 26%, and selectively to linear diacetate was nearly 20%. The ratios of linear to branched monoacetates and diacetates were both ~0.7 in this case.

EXAMPLE 12

Using the procedures of Example 5 except that the solvent was changed from 100% acetic acid to a 50/50 mixture of sulfolane and acetic acid, selectivity to linear diacetate exceeded 25% of reaction product. The ratio of branched to linear diacetates produced was ~1/1.

EXAMPLE 13

Using the procedures of Example 3 except that the solvent was changed from 100% acetic acid to a 50/50 mixture of dimethylacetamide and acetic acid, the ratio of linear monoacetate to branched monoacetate exceeded 1.2. High yields of the linear 1,4-diacetates were also obtained.

EXAMPLE 14

Using the procedures of Example 3 except that 1-butene was used instead of cis-2-butene, the linear allylic monoacetate yield was 34%, the branched monoacetate yield was 26% and linear 1,4-diacetates were produced in nearly 20% selectivity.

EXAMPLE 15

Using the procedures of Example 12 except that iso-butylene was used in place of cis-2-butene, both vinylic and allylic monoacetates as well as vinylic and allylic diacetates were formed in good yield.

What I claim is:

1. A process for the production of butene acetates and linear butene -1,4- diacetates which comprises first activating a supported palladium metal catalyst by contacting it with a $C_3$-$C_6$ olefin at a temperature of greater than about 50° C. for a period of time sufficient to provide at least a small but perceptible quantity of said activated catalyst, in the substantial absence of oxygen, and thereafter contacting the activated catalyst with acetic acid and cis-butene-2, trans-butene-2, or butene-1 admixed with air or oxygen in a liquid medium, thereby forming the corresponding butene acetates and linear butene-1,4-diacetates.

2. A process for the production of butene acetates and linear butene -1,4- diacetates which comprises first activating a supported palladium metal catalyst by contacting it with a butene selected from the group consisting of cis-butene-2, trans-butene-2, and butene-1 in a liquid medium at a temperature of at least about 60° C. for at least about 10 minutes, in the substantial absence of oxygen, and thereafter contacting the activated catalyst with acetic acid and the corresponding cis-butene-2, trans-butene-2, or butene-1 admixed with air or oxygen in said liquid medium, thereby forming the corresponding butene acetates and linear butene-1,4-diacetates.

3. The process of claim 1 or 2 wherein the catalyst is activated in the essential absence of oxygen.

4. The process of claim 1 or 2 wherein the catalyst is maintained in its activated state by continuous contact with the butene.

5. The process of claim 1 or 2 wherein the catalyst is activated with the butene under pressures of from about 1 to 100 atmosphere of said butene.

6. The process of claim 1 or 2 wherein the catalyst is activated with the butene at temperatures of from about 60° C. to 150° C. for at least about 10 to 120 minutes.

7. The process of claim 1 or 2 wherein the support for the palladium metal is carbon or alumina.

8. The process of claim 1 or 2 wherein the oxidation is carried out at temperatures of at least about 50° C.

9. The process of claim 1 or 2 wherein the oxidation is carried out with not greater than approximately stoichiometric amounts of the oxygen needed to produce said corresponding butene acetates and diacetates.

10. The process of claim 1 or 2 further comprising carrying out the oxidation in the presence of the solvent dioxane, sulfolane, or dimethylacetamide.

11. The process of claim 1 or 2 wherein the oxidation is carried out in the presence of a metal acetate.

12. A process for the production of butene acetates and linear butene-1,4-diacetates which comprises oxidizing cis-butene-2, trans-butene-2, or butene-1 admixed with air or oxygen in the presence of acetic acid and an activated palladium metal catalyst in a liquid medium, wherein said catalyst was previously activated by contacting a supported palladium metal catalyst with a $C_3$-$C_6$ olefin at a temperature of greater than about 50° C. for a period of time sufficient to provide at least a small but perceptible quantity of said activated catalyst, in the substantial absence of oxygen.

13. A process for the production of butene acetates and linear butene-1,4-diacetates which comprises oxidizing cis-butene-2, trans-butene-2, or butene-1 admixed with air or oxygen in the presence of acetic acid and an activated palladium metal catalyst in a liquid medium, wherein said catalyst was previously activated by contacting a supported palladium metal catalyst in a liquid medium with a butene corresponding to the one to be oxidized at a temperature of at least about 60° C. for at least 10 minutes in the substantial absence of oxygen.

14. The process of claim 12 or 13 wherein the catalyst is activated in the essential absence of oxygen.

15. The process of claim 12 or 13 wherein the catalyst is maintained in its activated state by continuous contact with the butene.

16. The process of claim 12 or 13 wherein the support for the palladium metal is carbon or alumina.

17. The process of claim 12 or 13 wherein the oxidation is carried out with not greater than approximately stoichiometric amounts of oxygen needed to produce said corresponding butene acetates and diacetates.

18. The process of claim 12 or 13 wherein the catalyst is activated with the butene under pressures of from about 1 to 100 atmosphere of said butene.

19. The process of claim 12 or 13 wherein the catalyst is activated with the butene at temperatures of from about 60° C. to 150° C. for at least about 10 to 120 minutes.

20. The process of claim 12 or 13 wherein the oxidation is carried out at temperatures of at least about 50° C.

21. The process of claim 12 or 13 further comprising carrying out the oxidation in the presence of the solvent dioxane, sulfolane, or dimethylacetamide.

22. The process of claim 12 or 13 wherein the oxidation is carried out in the presence of a metal acetate.

23. The process of claim 1 or 12 wherein the $C_3$-$C_6$ olefin is a butene.

24. The process of claim 1 or 12 wherein the activation is carried out at a temperature of at least about 55° C.

25. The process of claim 1 or 12 wherein the activation is carried out in a liquid medium.

26. The process of claims 1 or 2 wherein the catalyst is activated in the presence of acetic acid.

27. The process of claims 12 or 13 wherein the catalyst was activated in the presence of acetic acid.

28. The process of claims 1, 2, or 13 wherein the reaction is carried out in the added presence of a solvent.

* * * * *